US008414831B2

(12) United States Patent
Jayatissa (10) Patent No.: US 8,414,831 B2
(45) Date of Patent: Apr. 9, 2013

(54) CHLORINE GAS SENSING SYSTEM

(75) Inventor: Ahalapitiya H. Jayatissa, Sylvania, OH (US)

(73) Assignee: The University of Toledo, Toledo, OH (US)

( * ) Notice: Subject to any disclaimer, the term of this patent is extended or adjusted under 35 U.S.C. 154(b) by 852 days.

(21) Appl. No.: 12/482,024

(22) Filed: Jun. 10, 2009

(65) Prior Publication Data

US 2011/0297541 A1 Dec. 8, 2011

Related U.S. Application Data

(60) Provisional application No. 61/060,871, filed on Jun. 12, 2008.

(51) Int. Cl.
*G01N 21/00* (2006.01)
(52) U.S. Cl. ....... 422/88; 422/425; 422/426; 422/82.05; 422/83; 438/34; 438/104; 977/700; 977/712; 977/720; 977/721; 977/722; 977/723; 977/742; 977/810; 977/811; 977/921; 436/124
(58) Field of Classification Search ............. 422/425, 422/426, 82.05, 83, 88; 438/34, 104; 977/700, 977/712, 720, 721, 722, 723, 742, 810, 811, 977/921; 436/124
See application file for complete search history.

(56) References Cited

U.S. PATENT DOCUMENTS

| 6,096,560 | A  | * | 8/2000 | Scripca et al. | ........... 436/164 |
| 7,276,389 | B2 | * | 10/2007 | Kim et al. | ........... 438/34 |
| 7,723,684 | B1 | * | 5/2010 | Haddon et al. | ........... 250/338.1 |
| 2007/0145356 | A1 | * | 6/2007 | Amlani et al. | ........... 257/40 |

OTHER PUBLICATIONS

Cantalini et al., "Gas sensing properties of nanocrystalline NiO and Co3O4 in porous silica sol-gel films", Sensors and Actuators B 108 (2005) 184-192.*
Kumar et al., Carbon Nanotubes From Camphor: An Environment-Friendly Nanotechnology, Journal of Physics, 2007, 643-646, Conference Series 61.
Inami et al., Synthesis-Condition Dependence of Carbon Nanotube Growth by Alcohol Catalytic Chemical Vapor Deposition Method, Science and Technology of Advanced Materials 8, 2007, 292-295.
Beckman, UC Researchers Shatter World Records With Length of Carbon Nanotube Arrays, University of Cincinnati, Apr. 27, 2007, 1-3.
Pending U.S. Appl. No. 09/063,533, filed Mar. 9, 2009. This Case Has a Common Inventor.

* cited by examiner

*Primary Examiner* — Jill Warden
*Assistant Examiner* — Monique Cole
(74) *Attorney, Agent, or Firm* — MacMillan, Sobanski & Todd, LLC (57) ABSTRACT

A chlorine gas sensor system includes carbon nanotubes at least partially coated with a metal oxide deposited on a substrate, and a source of infra-red light positioned to illuminate at least a portion of the coated nanotubes.

14 Claims, 8 Drawing Sheets

CHLORINE GAS SENSING SYSTEM

CROSS-REFERENCE TO RELATED APPLICATIONS AND STATEMENT REGARDING SPONSORED RESEARCH

The present invention claims the benefit of the provisional patent application Ser. No. 61/060,871, filed Jun. 12, 2008.

This invention was made with government support under grants from NSF Grant No. ECS-0401690 and DARPA Grant No. HR0011-07-0003. The government has certain rights in this invention.

TECHNICAL FIELD

There is disclosed herein a system for sensing chlorine gas without the need for heating.

BACKGROUND OF THE INVENTION

There is no admission that the background art disclosed in this section legally constitutes prior art.

Carbon nanotubes (CNTs) have attracted worldwide attention because of their distinctive mechanical, chemical and electronic properties. Recently, CNT-based gas sensors [2-10] have received considerable attention because of their outstanding properties such as a faster response, higher sensitivity, and lower operating temperature. CNT gas sensor successfully detected ppm level $H_2$, $NO_2$, $CO_2$, $O_2$ and $NH_3$. In a slightly different mechanism, dielectric phoresis impedance analysis 3, $F_2$, $NH_2$, and $NO_2$ has been detected. These CNT based sensors have advantages over metal oxides due to detection capability in room temperature. The CNTs have attracted great interest for use as gas sensors mainly due to their large surface area, high electrical conductivity and chemical stability while the surface reacts with gas molecules [10-14]. CNT-based sensors have been investigated for the detection of gases of [15-20] as well as of other chemicals like organic compounds [21,22]. Both single-wall carbon nanotubes (SWNTs) and multi-wall carbon nanotubes (MWNTs) have been used as the sensing probes. For device fabrication, either CNTs were directly synthesized on substrates via chemical vapor deposition (CVD), or the collected CNT powders were pasted on substrates. In some cases, carbon nanotubes have been modified by coating a catalytic metal particles, metal oxides and organic materials to enhanced selectivity of particular gas. For instance, $SnO_2$ were coated by vacuum evaporation method to detect Co selectively, while Pd clusters were coated on nanotube surfaces by a wet chemical method to enhance hydrogen detection capability.

Chlorine gas is widely used as effective whiteners and disinfectors in many industrial processes such as paper, fabric, water purification and food production [2-5]. Chlorine is very harmful when emitted into the environment. In small amounts, chlorine and chorine dioxide exist in the atmosphere and are ozone-decomposing impurities [1]. Moreover, chlorine is one of the constituent elements of toxic dioxin. Chlorine containing compounds have been used as chemical weapons throughout history. Thus, the problem of the rapid determination of chlorine and chlorine dioxide in the air at the level of their maximum permissible concentrations, 1 and 0.1 mg/m, respectively, is important. Though highly useful, detection of a trace amount of chlorine is very important to avoid environmental destruction and safety purposes. Also, in order to monitor emission of chlorine gases to the environment, continuous detection capability is important.

Several solid state electrochemical sensors have been developed for the measurement of low chlorine concentrations. These sensors operate at relatively high temperatures and use metal chlorides and AgCl/Ag-β"-alumina as the solid electrolyte. The emf obtained with such devices in chlorine-free environments remains high, and Nerstian responses are impossible to obtain for partial pressures less than 10.5 atm.

The design and testing of a chlorine gas potentiometric gauge, using SrCl/KCl as the electrolyte have also been reported. Though this sensor can detect lower concentrations in 10 ppm range in conventional diluting gases such as air, argon, oxygen and nitrogen, the sensor operates between 120 and 400° C. which cause some difficulty in continuous monitoring.

Also, marketed versions of instruments for chlorine measurement already exist and are very effective for high concentration of chlorine, in the range of 1-10.4 atm. These spectrophotometric UV devices operate in continuous mode at room temperature and with excellent reliability. Their high costs may, however, prevent their use in certain installations.

There are a few approaches to develop chlorine sensors using metal oxide semiconductors. Among these metal oxides, commonly used materials are $SnO_2$, ZnO and $WO_3$ have been tested in practical testing devices. It is believed that a resistance decrease in semiconductor gas sensors exposed to inflammable gases results from desorption of oxygen adsorbed on the surface and grain boundaries of metal oxides at high temperatures in the air. However, this sensing mechanism is not expected in the detection of chlorine gas. In addition, Chlorine gas may corrode metal oxides at high temperatures in air because of the HCl resulting from the chemical reaction with the water in air.

Therefore, for the practical use of chlorine semiconductor gas sensors, it is necessary to develop sensor materials with high sensitivity as well as high stability.

In order to stabilize metal oxides in chlorine ambient, multicomponent oxides-based gas sensors were developed. However, these sensors could detect chlorine only above 250° C.

In resistive sensors, phthalocyanine films have been investigated. Though these sensors have high sensitivity down to ppm level, the stability of these polymer films were very poor under elevated temperatures compared with metal oxides.

Other detection methodologies include gas chromatography and chemical analytical methods which requires time, expertise and costly instrumentations. Also, these detection methods cannot be used for continuous monitoring of ambient at multiple places rapidly.

As discussed above, there is a growing demand for efficient detection methods of chlorine gas. It is desired that this method be cost effective, easy to operate and reliable. Though UV spectroscopy based detection method has been commercialized, the use of such devices in outdoor applications, environmental monitoring and online detection is difficult.

Another method used metal oxide based-sensors in order to attempt to provide a low cost and simple detection of hazardous level of chlorine leakages. The disadvantage of such detection method is the heating requirement that reduces the lifetime of the sensors at elevated temperatures. Due to the same heating requirements, operational costs of these sensors continue to make monitoring difficult. Another difficulty is that change of batteries makes inconvenient to use metal oxide sensors.

Therefore, development of gas sensors for rapid monitoring of ambient environments using an inexpensive and straightforward method is required.

Various objects and advantages of this invention will become apparent to those skilled in the art from the following detailed description of the preferred embodiment, when read in light of the accompanying drawings.

SUMMARY OF THE INVENTION

In a broad aspect, there is provided herein a chlorine gas sensor that does not require heating. The sensor consists of metal oxide coated carbon nanotubes. Non-limiting example of metal oxide include tin oxide, tungsten oxide, zinc oxide, palladium oxide, nickel oxide or titanium oxides. Other useful oxides can include vanadium, copper, molybdenum, gallium, and cadmium. This improved gas sensors modifies bare carbon nanotubes which are sensitive only for several gases in room temperature. In the presently disclosed system, the sensitivity of carbon nanotubes was enhanced by surface modification. In one embodiment, the carbon nanotubes were modified by coating an ultra-thin tungsten oxide layer onto the carbon nanotubes. The ultra-thin tungsten oxide layer selectively enhances the sensing of chlorine gas. In certain embodiments, infra-red (IR) light is used to enhance the recovery speed of gas sensors.

These and other objects, features and advantages of the invention will become apparent to those skilled in the art from a reading of the detailed description and claims set forth below together with the drawings as described below.

DETAILED DESCRIPTION OF THE PREFERRED EMBODIMENT(S)

Described herein in a chlorine gas sensor which does not have a heating requirement in order for the sensor to be "reset" after exposure to gases.

The chlorine gas sensor includes an ultra-thin layer of a metal oxide coated on carbon nanotubes. The substrates can be any insulators such as glass, silicon nitride or silicon dioxides coated substrates, ceramic substrates such as alumina.

In one non-limiting embodiment; tungsten oxide was selected since tungsten oxide has high selectivity for chlorine gases. Non-limiting example of metal oxide include tin oxide, tungsten oxide, zinc oxide, palladium oxide, nickel oxide or titanium oxides. Other useful oxides may include vanadium, copper, molybdenum, gallium, and cadmium.

Achieving fast response and fast recovery time of these gas sensors is important. In many cases, although nanotube based sensors possessed fast sensitivity at room temperature without extra heating, their recovery time is as long as few hours. In order to overcome this problem, the present invention provides a technique to enhance the response time by irradiation of the sensor filament with a light beam (infrared, visible, or UV).

The chlorine gas sensor is fabricated on a MEMS based insulating deprograms so that all the components of the chlorine gas sensor can be integrated to optimize the operational conditions.

Figure 1:
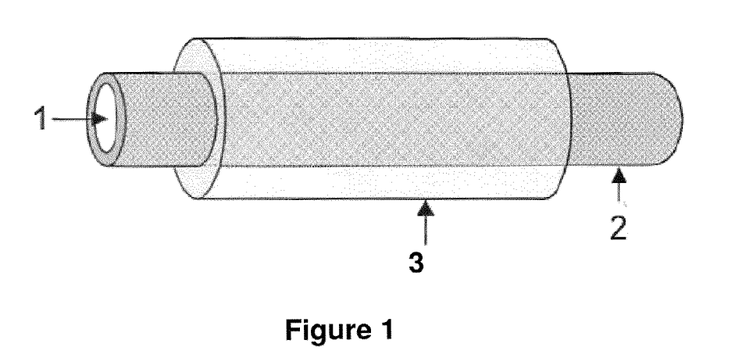
FIG. 1 is a schematic illustration of a multi-wall nanotube having a coating of a metal oxide layer.

FIG. 1 is a schematic illustration of a nanotube 1 having an outer surface 2 and a substantially uniform coating of a metal oxide layer that is co-axially coated on at least a portion of the length of the carbon nanotube.

Figure 2:
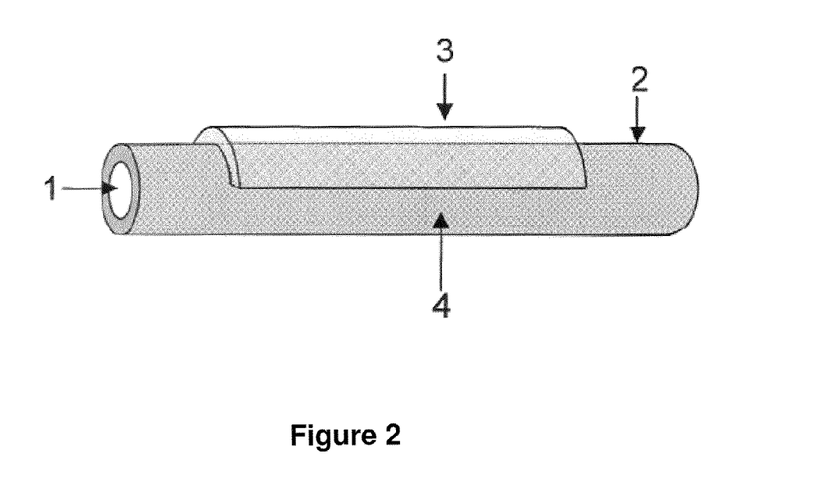
FIG. 2 is a schematic illustration of a multi-wall nanotube having a coating of a metal oxide layer that is coated on at least a portion of the length of the carbon.

FIG. 2 is a schematic illustration of a nanotube 1 having an outer surface 2 and a substantially uniform coating of a metal oxide layer that is coated on at least a portion of the length of the carbon nanotube 1. The carbon nanotube 1 also has an uncoated shadow area 4.

Figure 3A:
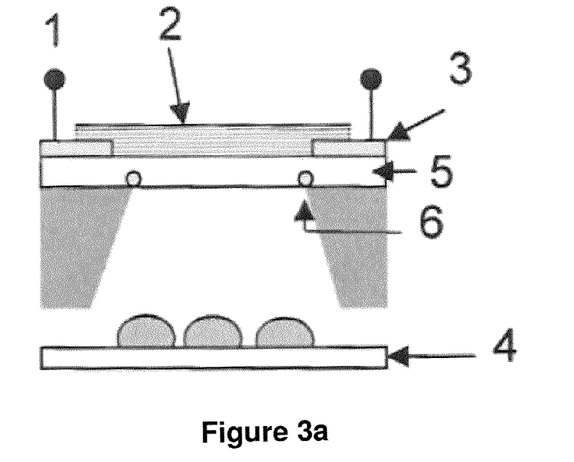
FIG. 3a is a schematic illustration of a sensor structure.

FIG. 3a is a schematic illustration of a sensor structure 110 that includes sensor terminals 111a 111b, a functionalized CNT layer 112 having a front side 112a and a back side 112b, electrodes 113a, 113b (for example, Au electrodes), an LED array 114 (having LEDs 117), a SiNx membrane 115, and a thermocouple 116.

In another embodiment, the CNTs 112 are coated on the SiNx membranes 115 using a free fabrication process. Free fabrication can be done as (i) direct synthesis of CNT 112 between electrodes 113a, 113b on substrates comprised of the SiNx membrane 115, electro-deposition of carbon nanotubes, dip-immersion of electrodes fabricated substrate in a CNT containing solution, spin coating of carbon nanotube containing liquid, place a drop of CNTs+organic liquid followed by evaporation.

The IR light emission diode (LED) array 114 is connected (not shown) to the backside 110b of the sensor structure 110, and the CNTs 112 are irradiated through the SiNx membrane 115. The on/off states of the LED array 114 can be fixed at the Rmin/Rmax, respectively. When any chlorine gas is passed through the sensor structure 110, the resistance changes from $R_{max}$ to the saturation level ($R_{min}$). At this point, the backside 112b of CNTs 112 is irradiated by the LED array 114. Subsequently, any adsorbed chlorine gas releases from the upper surface 112a of the CNTs 112. The circuitry (schematically illustrated in FIG. 3b) is designed to turn off the LED array 114 when the resistance reaches $R_{max}$.

In the embodiment shown in FIG. 3a, functionalized CNTs 112 are located on the SnNx membrane 115 between Au electrodes 113a, 113b. The IR LED (array) 114 is placed at the SiNx membrane 115 so the backside 112b of the CNTs 114 can be irradiated with IR light.

Figure 3B:
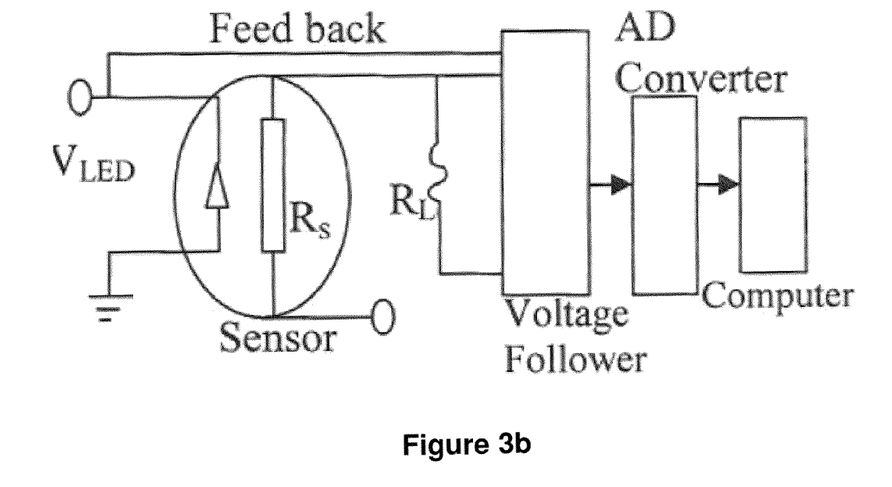
FIG. 3b is a schematic illustration of a suitable interface circuit diagram of a resistive gas sensor.

FIG. 3b is a schematic illustration of a suitable interface circuit 120 for the resistive gas sensor structure 110, the interface circuit 120 generally having a feed back loop 112, a voltage follower 124 connected to an AD converter 126 which, in turn is connected to a computer 128.

Examples of Working Capability of Sensor

Figure 4A:
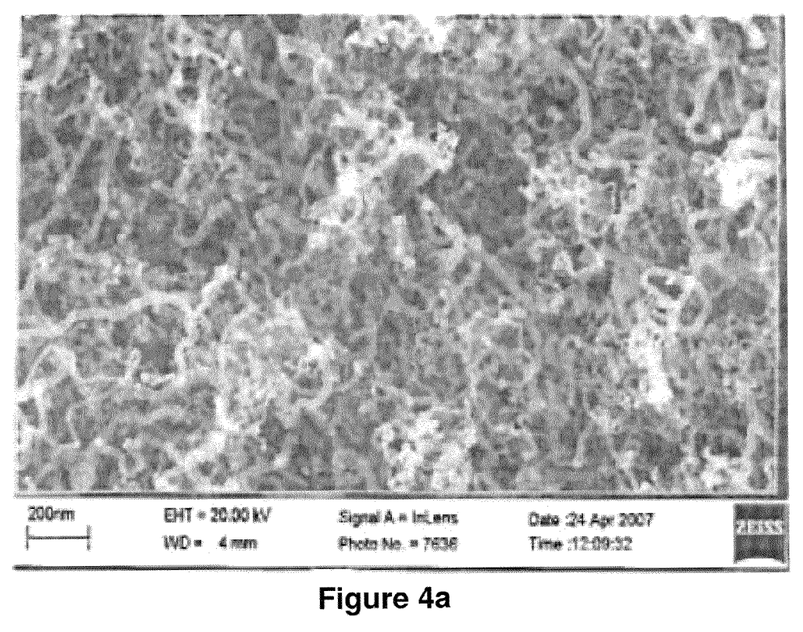
FIGS. 4a-c are SEM images of multi-wall carbon nanotubes (CNTs) without coating a metal oxide layer FIG. 4a) and with ultra-thin metal oxide layers (FIGS. 4b, 4c).
Figure 4B:
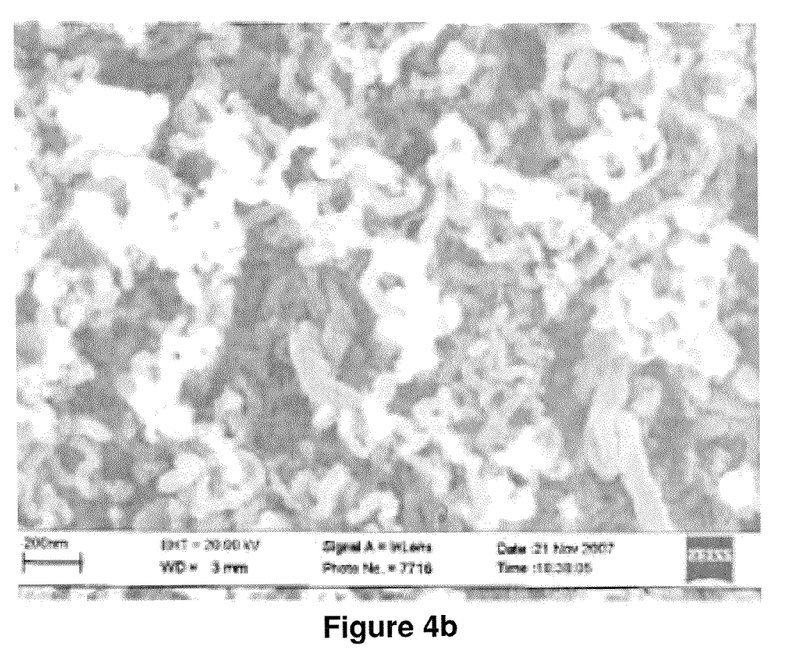
Figure 4C:
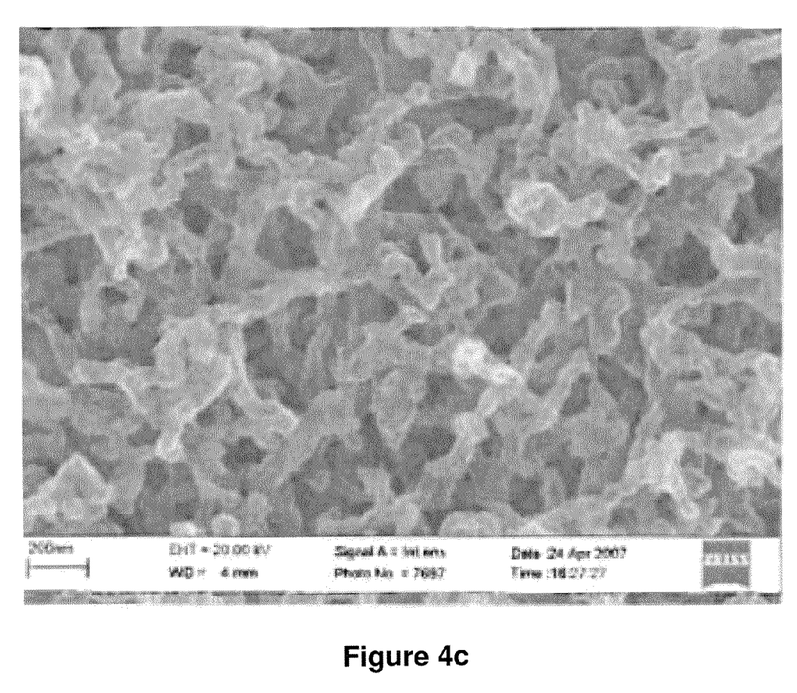

FIGS. 4a-c show the SEM images of CNTs without coating a metal oxide and with an ultra-thin metal oxide layers. FIG. 4a is a SEM image of CVD synthesized CNT as-deposited sample.

The vacuum coated films shown in FIG. 4b have a less conducting layer than the chemical bath coated films shown in FIG. 4c. FIG. 4c shows the CNTs after coating a metal oxide layer by wet chemical bath method using ammonium tungstate and NaOH.

As shown in FIG. 4b, the upper portion of vacuum coated metal oxide CNTs have more bright spots because of conductivity difference in SEM. The chemical bath coated oxide materials shown in FIG. 4c have a grain like morphology on the surface. The chemical bath method crystallites are nucleated on the surface. In the vacuum evaporation method shown in FIG. 4b, the films are coated uniformly on the top side of nanotubes.

Sensor Characteristics

Figure 5:
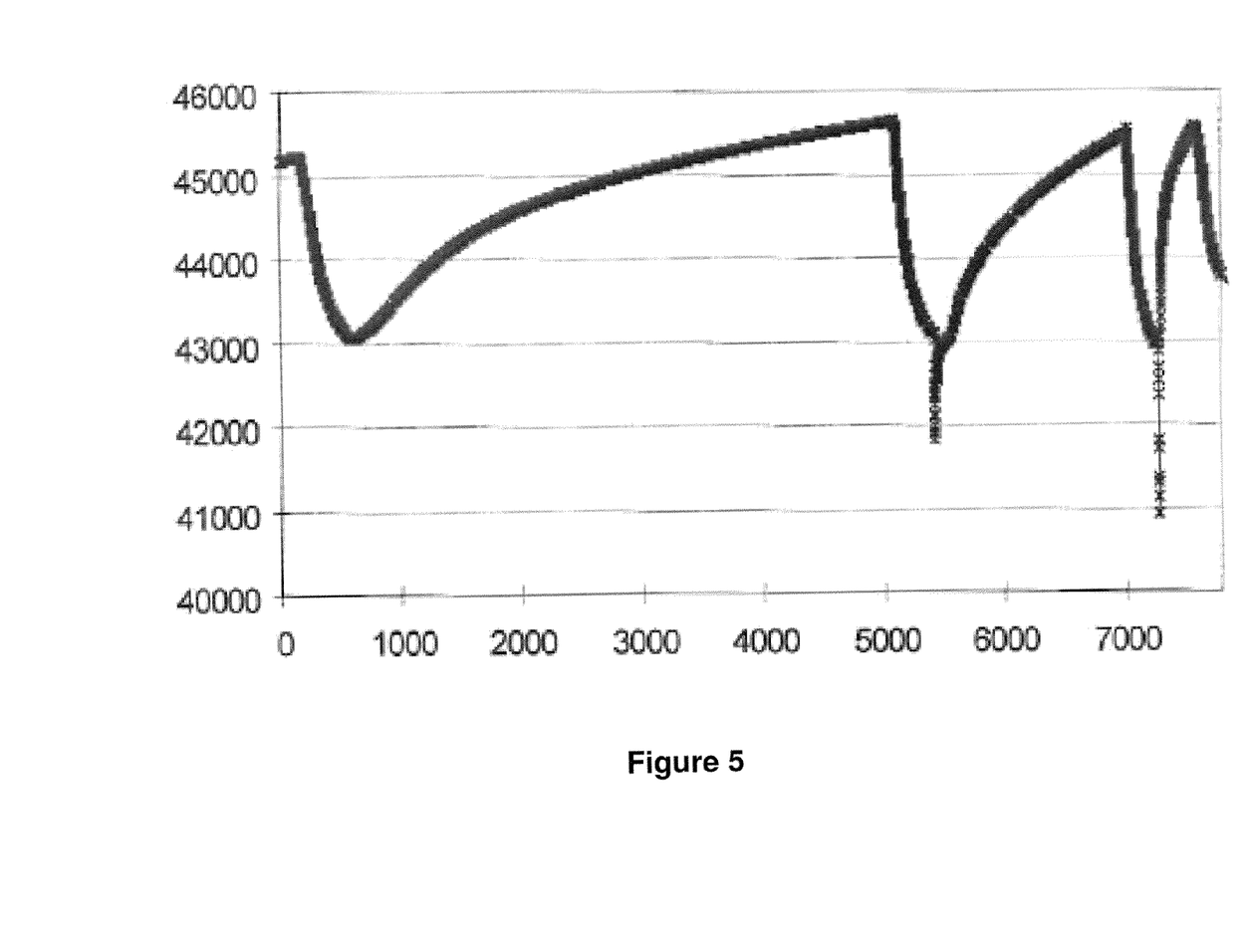
FIG. 5 is a graph showing the sensor characteristics of metal oxide coated CNTs for 5 ppm chlorine gas in air at room temperature.
Figure 6:
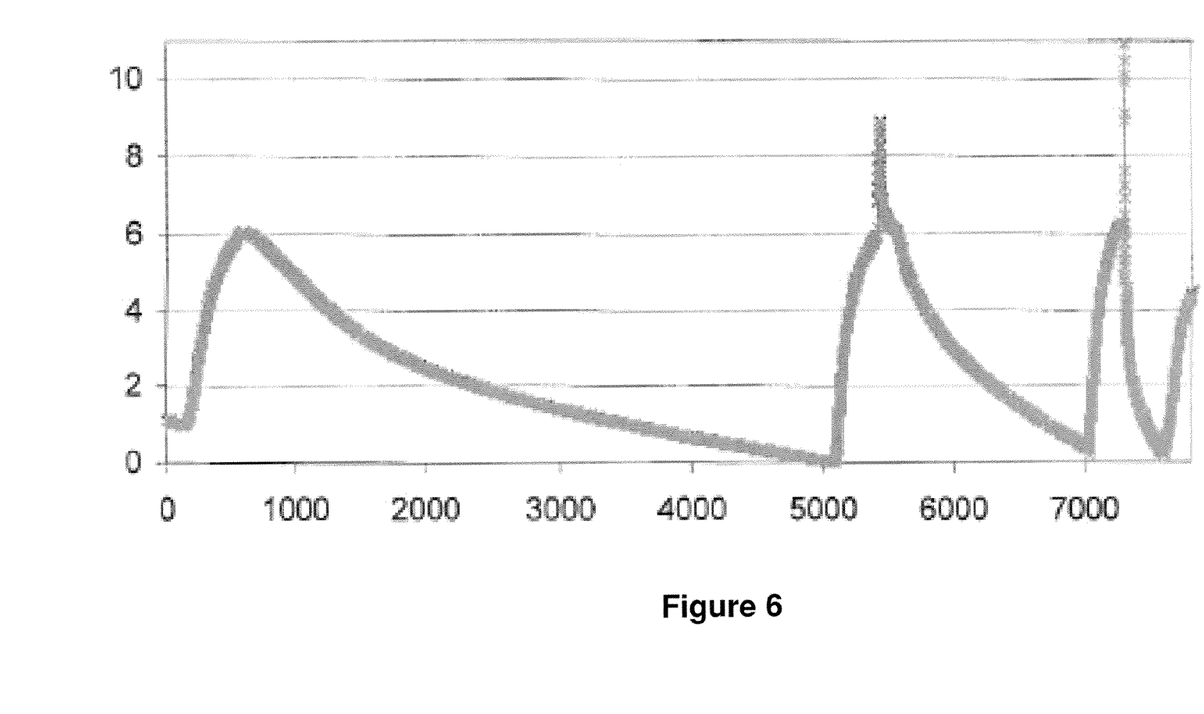
FIG. 6 is a graph showing the sensor characteristics as sensitivity (5 ppm) in air.

FIG. 5 is a graph showing the sensor characteristics of tungsten oxide coated CNTs for 5 ppm chlorine gas in air at room temperature. FIG. 6 is a graph showing the sensor characteristics as sensitivity (5 ppm) in air.

The sensing properties of these coated films for chlorine gas are given in FIG. 5 and FIG. 6. It can be seen that the vacuum coated films (FIG. 5) have a slower response for gases than for chemical bath coated films (FIG. 6). However, recovery time is faster for vacuum evaporated films. When IR light irradiated the coated films, the recovery time was improved; for vacuum coated films it was two times faster than for chemically coated films. These tests clearly indicate that the vacuum evaporated films absorb more IR light because the tungsten oxide layer was coated on only one layer. Moreover, the bandgap of tungsten oxide (–3.1 eV, $\lambda=322$ nm) layer is much higher than these laser beams (a, =632 nm). The gas sensor described herein provides an improved sensor performance. In particular, recovery time by irradiation with IR light provides a rapid response and a rapid recovery sensor.

As described herein, a metal oxide modified CTS was successfully synthesized using a chemical vapor deposition (CVD) process. In addition, the tungsten oxide layers were uniformly coated in both vacuum evaporation method and chemical bath method. The metal oxide coated CNTS were sensitive for chlorine at unheated (not room temperature) conditions.

Example of Sensor Stability

The stability of the sensor was measured at humidity levels of 50% for three months. The sensor signal was changed only for +/−2%. When higher humidity was used, the sensor signal was increased about +2%. This effect was independent of chlorine concentration.

Furthermore, when the sensor signal was measured in air (i.e., no chlorine) with 20% and 50% humidity, the sensor signal goes to opposite direction, thus indicating that sensor described herein has a higher selectivity for chlorine than water wiper Examples of Carbon Nanotubes It is within the contemplated scope of the present invention that different types of nanotubes and methods for making them can be used.

Figure 7:
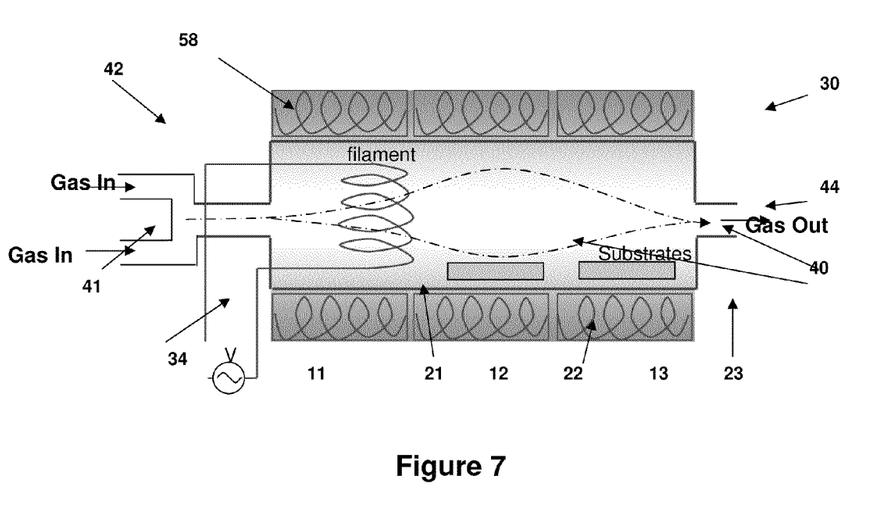
FIG. 7 is a schematic illustration of a chemical vapor deposition (CVD) system for forming carbon nanotubes.
Figure 8:
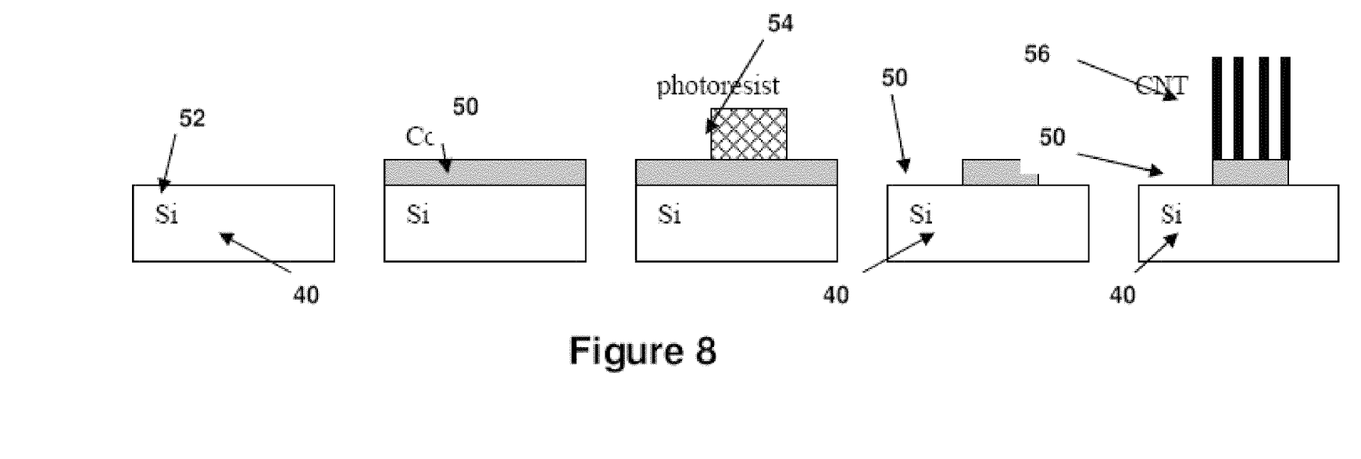
FIG. 8 is a series of schematic illustrations showing steps in a process for forming carbon nanotubes on a substrate.
Figure 9:
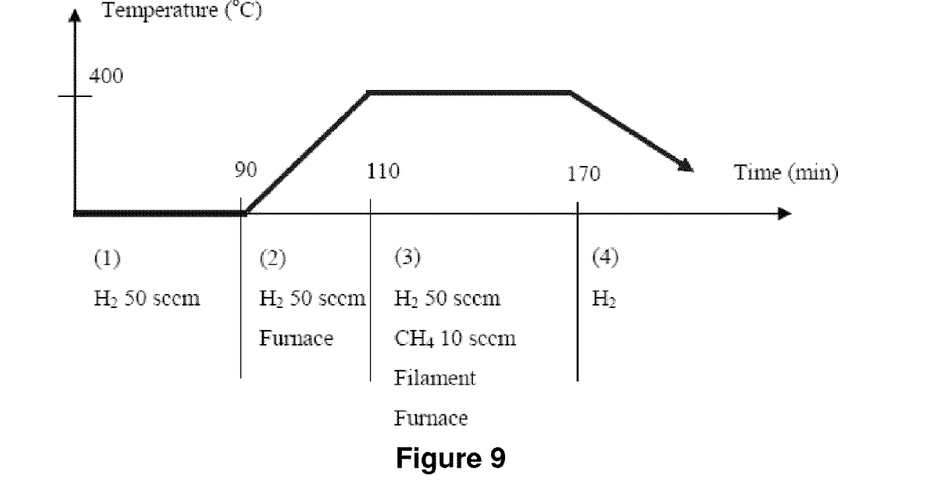
FIG. 9 is a schematic illustration showing the temperatures and times sequences for forming carbon nanotubes on a substrate.

In one non-limiting example, a method for forming carbon nanotubes can be as shown by referring to FIGS. 7, 8 and 9.

Referring now to FIG. 7, a hot filament CVD system 8 includes a furnace 10 having multiple heating zones, here showing first, second and third heating zones 11, 12 and 13, respectively. In one embodiment, the hot filament CVD system 10 can be a Lindberg/Blue 3-Zone Tube furnace 10 where the first, second and third heating zones 11, 12 and 13, respectively, are surrounded by three groups of heating coils 21, 22 and 23, respectively. The furnace 10 includes a quartz tube 30 which extends through the heating zones 11, 12 and 13. The furnace includes a filament 32, and a power supply 34.

The three groups of heating coils 21, 22, 23 can be separately programmed to heat each zone 11, 12 and 13, respectively of the furnace 10 at specific times and at specific temperatures. In one embodiment, a UP150 Program Temperature Controller can be used. A small quartz frame (not shown) can be placed in the quartz tube 30 to hold one or more substrates 40. In certain embodiments, the substrate 40 can be, for example, a silicon or glass substrate.

The furnace 10 includes a first gas inlet 41 for supplying a feed gas, such as methane, and a second gas inlet 42 for supplying a carrier gas, such as hydrogen or argon into the quartz tube 30. The furnace 10 includes at least one gas outlet 44 at an opposing end of the quartz tube 30 through which the reaction gases are exhausted.

The filament 32 is positioned in proximity to the first and second gas inlets 41 and 42 such that the filament 32 heats the feed gas and carrier gas as they are being injected into the furnace 10. In certain embodiments, the filament 32 can comprise a tungsten wire of 0.5 mm in diameter and 30 cm in length that is shaped into a coil.

The power supply 34 supplies energy (e.g., by applying about 10V voltage by an AC power regulator), to the filament 32. In certain embodiments, the filament 32 is heated to about 2000° C., and the color of filament 32 changes from red to white. The carrier gas and feed gas are mixed and passed into the quartz tube 30. When the gases pass through the hot filament 32, the carrier gas is decomposed into carbon radical species and hydrogen. The carrier gas then carries the carbon radical species to the substrate wherein carbon nanotubes 56 (see FIG. 7) are formed or grown on the substrate 40.

Growth of Carbon Nanotubes

FIG. 7 is a schematic illustration of the process for growing carbon nanotubes on a substrate 40. In certain embodiments, the substrate 40 can include a suitable catalyst 50 coated on at least a top surface 52 of the substrate. In certain embodiments, the catalyst 50 can be deposited in a desired pattern on the top surface 52 of the substrate 50.

In the embodiment shown in FIG. 7, the processes to grow carbon nanotubes include: (a) providing a substrate 40, (b) coating the substrate 40 with a catalyst 52 using a physical vapor deposition (PVD) process, (c) etching using photolithography, (d) forming a suitable pattern made by etching the catalyst 52, and (e) growing carbon nanotubes 56 on the catalyst 52 using a chemical vapor deposition (CVD) process.

In one embodiment, the substrates for growing the carbon nanotubes 56 can include silicon wafer and glass substrates 40, coated with a suitable metallic catalyst 52, such as cobalt (Co), nickel (Ni) or iron (Fe). The metallic catalyst 52 can be coated on the silicon wafer or glass substrate 40 by a suitable physical vapor deposition (PVD) process. In certain embodiments, depending on the amount of catalyst wire (not shown) used in the physical vapor deposition (PVD) process and the distance between the silicon wafer or glass substrate 40 and the catalyst wire (not shown) being used in the PVD of the catalyst 50, the thickness of the catalyst film 50 coated on substrate 40 can range from about 0.5 nm to about 50 nm.

The substrate 40 is positioned at the far end (third zone 13) of quartz tube 30. A cap 58 operatively connected to gas inlets 41 and 42, the filament 32 and the power supply 31 is connected to the quartz tube 30 to seal the first end of the quartz tube 30.

In one embodiment, the heating progress was set by programming the UP150 Program Temperature Controller such that the temperatures of zone 1 and 2 were set at 500° C., and the temperature of zone 3 was 400° C. After starting the nanotube 56 growth process, the CVD furnace 10 is heated according to a desired setting of time and temperatures, and the gases are injected into the quartz tube 32 according to the desired progress of the growth of the nanotubes 56.

One nanotube growth sequence useful to grow carbon nanotubes is shown in FIGS. 8 and 9. In one embodiment, for example, the sequences of growing carbon nanotubes includes:

(1) injecting $H_2$ @ 50 sccm for 90 minutes in a clean CVD quartz tube 30;

(2) injecting $H_2$ @ 50 sccm, and heating furnaces to 500° C. in zones 11 and 12, and to 400° C. in zone 13) (where the substrate and furnace are preheated);

(3) applying power to the filament 32, for example, 10V~15V voltage to a tungsten filament until the filament turns from red and approached white color and/or the filament temperature is about 1500° C.~2000° C.); injecting carrier gas (for example, $H_2$ 50 sccm) and feed gas (for example, $CH_4$ 10 sccm) into the quartz tube 30, and maintaining furnace temperatures in the zones 11, 12 and 13 for a desired period of time (for example, for about 0.5~1.5 hours);

(4) turning off power (and, thus heat from) the filament 32 and heating zones 11, 12 and 13 in the furnace 12; ceasing injection of the feed gas (e.g., $CH_4$); and continuing injection of the carrier gas (e.g., $H_2$) until the temperatures within the first, second and third heating zones 11, 12 and 13 are cooled down (in some embodiments cooling to about to room temperature).

In order to compare the growth of carbon nanotubes 56 at lower temperatures to the growth of nanotubes at higher temperatures, the experiment was repeated at the same condition by changing only the temperature of reaction area (zone 3) to 500° C., 600° C., 700° C., 800° C. and 900° C. In other embodiments, the catalyst can comprise one or more of Co, Fe and Ni for growing carbon nanotubes.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated by reference herein, and for convenience are provided in the following bibliography.

Citation of any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

References

1. W. Schmidt, Using Chlorine Dioxide for Drinking Water Disinfection by the Application of the Chlorite/Chlorine Process, *Acta hydrochimica et hydrobiologica,* 32 (2004) 48-60.
2. B. Barbeau, R. Desjardins, C. Mysore, and M. Prevost, Impacts of water quality on chlorine and chlorine dioxide efficacy in natural waters, *Water Research,* 39 (2005) 2024-2033.
3. R. K. Gangopadhyay, and S. K. Das, Chlorine emission during the chlorination of water case study Environmental Monitoring and Assessment, 125 (2007) 197-200.
4. P. H. Dyke and G. Amendola, Dioxin releases from US chemical industry sites manufacturing or using chlorine, *Chemosphere,* 67 (2007) S125-S134.
5. P. J. Delaquis, L. R. Fukurnoto, P. M. A. Toivonen, and M. A. Cliff,
Implications of wash water chlorination and temperature for the microbiological and sensory properties of fresh-cut iceberg lettuce, *Postharvest Biology and Technology,* 31 (2004) 81-91.
6. M. Nickmilder, S. Carbonnelle, and A. Bernard, House cleaning with chlorine bleach and the risks of allergic and respiratory diseases in children, *Pediatric Allergy and Immunology,* 18 (2007) 27-35.
7. J. L. Heidt, G. B. Kistiakowsky, and G. S. Forbes, An Anomalous Decomposition of Ozone in the Presence of Chlorine, *Journal of the American Chemical Society,* 55 (1933) 223-231.
8. P. H. Dyke, and G, Amendola, Dioxin releases from US chemical industry sites manufacturing or using chlorine, *Chemosphere,* 67 (2007) S125-S134.
9. Y. Inuyama, C. Nakamura, T. Oka, Y. Yoneda, I. Obataya, N. Santo, and J. Miyake, Simple and high-sensitivity detection of dioxin using dioxin-binding pentapeptide, *Biosensors and Bioelectronics,* 22 (2007) 2093-2099.
10. A. Pelloux and C. Gondran, Solid state electrochemical sensor for chlorine and hydrogen chloride gas trace analysis, *Sensors and Actuators B: Chemical,* 59 (1999) 83-88.
11. A. Menne and W. Weppner, Selectivity, response time and chemical aspects of gas sensitive AgCl layers for gas sensors, *Solid State Ionics,* 40-41 (1990) 468-471.
12. J. Liu and W. Weppner, Limiting current type surface modified gas sensor based on bY-alumina fast solid ionic conductor, *Appl. Phys. A,* 52 (1991) 94-99.
13. B. Y. Liaw, J. Liu, and W. Weppner, Kinetics principles for new types of solid state ionic gas sensors, *Solid State Ionics,* 53-56 (1992) 18-23.
14. A. Menne and W. Weppner, Influence of moisture at solid gas interfaces in electrochemical Cl sensors, *Sensors and Actuators B,* 9 (1992) 79-82.
15. C. M. Mari, G. Terzaghi, M. Bertolini, and G. B. Barbi, A chlorine gas. potentiometric sensor, *Sensors and Actuators B,* 8 (1992) 41-45.
16. J. Mizsei, Semiconducting gas sensor incorporating a sparking decomposer, *Sensors and Actuators B,* 2 (1990) 199-203.
17. M. Miyama, A chlorine gas sensor using ceramic heterocontacts, *Chem. Sens.* 7 (1991) 9-13.
18. F. Bender, C. Kim, T. Mlsna, and J. F. Vetelino, Characterization of a WO3 thin film chlorine sensor, *Sensors and Actuators B: Chemical,* 77 (2001) 281-286.
19. T. Miyata, T. Hikosaka, and T. Minami, High sensitivity chlorine gas sensors using multicomponent transparent conducting oxide thin films, *Sensors and Actuators B: Chemical,* 69 (2000)16-21.
20. M. E. Azim-Araghi, and A. Krier, The influence of ammonia, chlorine and nitrogen dioxide on chloro-aluminium phthalocyanine thin films, *Applied Surface Science,* 119 (1997) 260-266.
21. S. Mubeen, T. Zhang, and Y. Ting, M. A. Deshusses, and N. V. Myung, Palladium nanoparticles Decorated Single- Walled Carbon Nanotube Hydrogen Sensor, *Journal of Physical Chemistry C*, 111 (2007) 6321-6327.
21. D. Ding, Z. Chen, S. Rajaputra, and V. Singh, Hydrogen sensors based on aligned carbon nanotubes in an anodic aluminum oxide template with palladium as a top electrode, *Sensors and Actuators: B. Chemical*, 124 (2007) 12-17.
22. L. Valentini, I. Armentano, J. M. Kenny, C. Cantalini, L. Lozzi, and S. Santucci, Sensors for sub-ppm $NO_2$ gas detection based on carbon nanotube thin films, *Applied Physics Letters*, 82 (2003) 961-963.
23. R. Wang, D. Zhang, W. Sun, Z. Han, and C. Liu, A novel aluminum-doped carbon nanotubes sensor for carbon monoxide, *journal of Molecular Structure*: THEOCHEM, 806 (2007) 93-97.
24. N. D. Hoa, N. Van Quy, Y. Cho, and D. Kim, An ammonia gas sensor based on non-catalytically synthesized carbon nanotubes on an anodic aluminum oxide template, *Sensors and Actuators: B. Chemical*, 127 (2007) 447-454.
25. Y. Lu, C. Partridge, M. Meyyappan, and J. Li, A carbon nanotube sensor array for sensitive gas discrimination using principal component analysis, *Journal of Electroanalytical Chemistry*, 593 (2006) 105110.
26. S. Chopra, K. McGuire, N. Gothard, A. M. Rao, and A. Pham, Selective gas detection using a carbon nanotube sensor, *Applied Physics Letters*, 83 (2003) 2280-2282.
27. R. Langlet, M. Arab, F. Picaud, M. Devel, and C. Girardet, Influence of molecular adsorption on the dielectric properties of a single wall nanotube: A model sensor, *The Journal of Chemical Physics*, 121 (2004) 9655-9665.
28. Y. X. Liang, Y. J. Chen, and T. H. Wang, Low-resistance gas sensors fabricated from multiwalled carbon nanotubes coated with a thin tin oxide layer, *Applied Physics Letters*, 85 (2004) 666-668.
29. C. H. Han, D. W. Hong, I. J. Kim, J. Gwak, S. D. Han, and K. C. Singh, Synthesis of Pd or Pt/titanate nanotube and its application to catalytic type hydrogen gas sensor, *Sensors and Actuators: B. Chemical*, 128 (2007) 320-325.
30. A. H. Jayatissa, A. Dadi, and T. Aoki, Nanocrystalline WO3 films prepared by two-step annealing, *Applied Surface Science*, 244 (2005) 453-457.
31. A. H. Jayatissa, S. T. Cheng, and T. Gupta, Annealing effect on the formation of nanocrystals in thermally evaporated tungsten oxide thin films, *Materials Science and Engineering*: B, 109 (2004) 269-275.
32. B. C. Liu, L. Z. Gao, Q. Liang, S. H. Tang, M. Z. Qu, and Z. L. Yu, A study on carbon nanotubes prepared from catalytic decomposition of C2H2 Or CH4 over the pre-reduced LaCoO3 perovskite precursor, *Catalysis Letters*, 71 (2001) 225-228.
33. G. Fang, Z. Liu, and K. L. Yao, Fabrication and Characterization of electrochromic nanocrystalline WO3/Si (111) thin films for infrared emittance modulation applications, *Journal of Physics D: Applied Physics*, 34 (2001) 2260-2266.

What is claimed is:

1. A chlorine gas sensor system comprising
carbon nanotubes at least partially coated with a metal oxide material deposited on a substrate, the metal oxide material being capable of absorbing chlorine gas at room temperature conditions, and
a source of infra-red light positioned to illuminate at least a portion of the coated nanotubes,
the source of infra-red light having on/off states at Rmin/Rmax, respectively, with R being resistance change, that respond to a presence of chlorine passing through the sensor structure, the on state being configured to provide infra-red light to the metal oxide material coated nanotubes sufficient to allow the adsorbed chlorine gas to release from metal oxide material coated carbon nanotubes, wherein, when chlorine passes through the sensor structure, the resistance changes from $R_{max}$ to ($R_{min}$), and the source of infra-red light is turned off when the resistance reaches $R_{max}$.

2. The system of claim 1, wherein the metal oxide material comprises one or more of oxides of: tungsten, tin, zinc, palladium, nickel, titanium, vanadium, copper, molybdenum, gallium, and cadmium.

3. The system of claim 1, including one or more sensor terminals and electrodes operatively connected to the substrate and operatively connected to an interface circuit.

4. The system of claim 1, wherein the source of infra-red light comprises an LED array.

5. The system of claim 1, wherein the carbon nanotubes comprise carbon nanotubes formed by growing carbon nanotubes using a hot filament CVD system.

6. The system of claim 1, wherein a catalyst is coated on the substrate prior to depositing the carbon nanotubes onto the substrate.

7. The system of claim 6, wherein the catalyst comprises one or more of cobalt, nickel and iron.

8. The system of claim 1, wherein a layer of a metal oxide is at least partially coated on the carbon nanotubes.

9. The system of claim 1, wherein the substrate comprises an insulator.

10. The system of claim 1, wherein the substrate comprises one or more of: glass, silicon nitride or silicon dioxides coated substrates, ceramic substrates, and alumina.

11. The system of claim 1, wherein the substrate comprises one or more of a silicon or glass substrate.

12. The system of claim 1, wherein the substrate comprises a SiNx membrane.

13. The system of claim 1, wherein the metal oxide material comprises $WO_3$ that is capable of absorbing chlorine gas a room temperature conditions.

14. The system of claim 3, wherein the interface circuit is configured to detect an interface charge transfer between the oxide metal material and the carbon nanotubes in the presence of the chlorine gas.

* * * * *